(12) United States Patent
Peng et al.

(10) Patent No.: US 11,833,486 B2
(45) Date of Patent: Dec. 5, 2023

(54) FUNCTIONALIZED NANOPARTICLES HAVING ENCAPSULATED GUEST CARGO AND METHODS FOR MAKING THE SAME

(71) Applicants: Berney Peng, Arlington, MA (US); Igor Sokolov, Medford, MA (US)

(72) Inventors: Berney Peng, Arlington, MA (US); Igor Sokolov, Medford, MA (US)

( * ) Notice: Subject to any disclaimer, the term of this patent is extended or adjusted under 35 U.S.C. 154(b) by 83 days.

(21) Appl. No.: 16/683,951

(22) Filed: Nov. 14, 2019

(65) Prior Publication Data

US 2020/0114329 A1    Apr. 16, 2020

Related U.S. Application Data

(63) Continuation-in-part of application No. 15/363,077, filed on Nov. 29, 2016, now abandoned.

(60) Provisional application No. 62/260,569, filed on Nov. 29, 2015.

(51) Int. Cl.
| | | |
|---|---|---|
| *B01J 13/16* | (2006.01) | |
| *A61K 9/51* | (2006.01) | |
| *C09K 11/02* | (2006.01) | |
| *A61K 31/704* | (2006.01) | |
| *C09K 11/06* | (2006.01) | |

(52) U.S. Cl.
CPC .......... *B01J 13/16* (2013.01); *A61K 9/5161* (2013.01); *A61K 9/5192* (2013.01); *A61K 31/704* (2013.01); *C09K 11/02* (2013.01); *C09K 11/06* (2013.01)

(58) Field of Classification Search
None
See application file for complete search history.

(56) References Cited

U.S. PATENT DOCUMENTS

| | | | |
|---|---|---|---|
| 2007/0059370 A1* | 3/2007 | Chou | A61K 9/5138 977/906 |
| 2008/0070319 A1* | 3/2008 | Makino | G01N 33/533 436/172 |
| 2010/0183731 A1* | 7/2010 | Miller | A61K 47/38 977/773 |
| 2011/0059142 A1* | 3/2011 | Papanicolaou | A61K 9/0051 977/840 |
| 2013/0136714 A1* | 5/2013 | Wang | A61K 9/0019 977/773 |

OTHER PUBLICATIONS

"Fluorescent Dyes" DayGlo. Accessed online on Aug. 12, 2021 at dayglo.com/products/dyes/fluorescent-dyes/. (Year: 2021).*

(Continued)

*Primary Examiner* — Carlos A Azpuru
*Assistant Examiner* — Casey S Hagopian
(74) *Attorney, Agent, or Firm* — Nadya Reingand

(57) ABSTRACT

This application discloses the approach of synthesizing cellulose acetate nanoparticles and rods which may have a chemically functionalized surface and an encapsulated cargo load. Functionalization and/or loading of the cargo are made through a physical mixing of the functionalizing and/or cargo components in the synthesizing bath. This can result in particles with functionalized surfaces with various functional groups, as well as active cargo load encapsulated in the particles. The encapsulated cargo includes but is not limited to biologically, chemically, and optically active substances.

2 Claims, 5 Drawing Sheets

(56) References Cited

OTHER PUBLICATIONS

Etsuo et al., Chapter 1: Vitamin E: Structure, Properties and Function, in Vitamin E: Chemistry and Nutritional Benefits, Royal Society of Chemistry, 2019, pp. 1-11. (Year: 2019).*

"Polar Protic and Aprotic Solvents", LibreTexts, 2021, accessed online on Dec. 13, 2021 at https://chem.libretexts.org/. (Year: 2021).*

Polyethylene glycol Product Information Sheet, Sigma-Aldrich, 2006, accessed online on Dec. 13, 2021 at https://www.sigmaaldrich.com. (Year: 2006).*

"Ultraviolet (UV) Radiation", UCAR, 2017, accessed online on Dec. 11, 2021 at https://scied.ucar.edu. (Year: 2017).*

"Infrared radiation", Britannica Online Encyclopedia, 2020, accessed online on Dec. 11, 2021 at https://wwww.britannica.com. (Year: 2020).*

"Quantum dots", Lateral Flows, 2019, accessed online on Dec. 11, 2021 at https://www.lateralflows.com. (Year: 2019).*

Robin, Y. Using Tocophersolan for Drug Delivery, Pharmaceutical Technology, Jan. 2, 2015, vol. 39, Issue 1, pp. 1-6. (Year: 2015).*

* cited by examiner

1. Preparation of a first medium

2. Preparation of a second medium

3. Adding the first medium to the second medium

4. Assembly of the particles via nanoprecipitation

5. Removal of the organic solvent

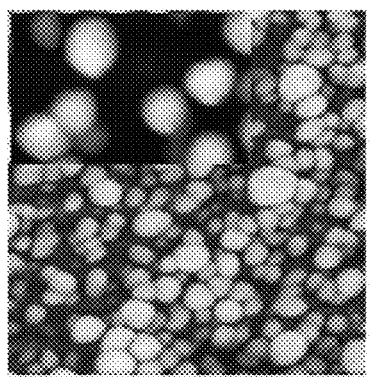
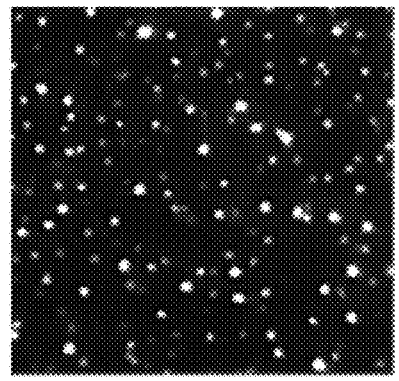
Fig. 3A　　　　　　　　　　　　Fig. 3B
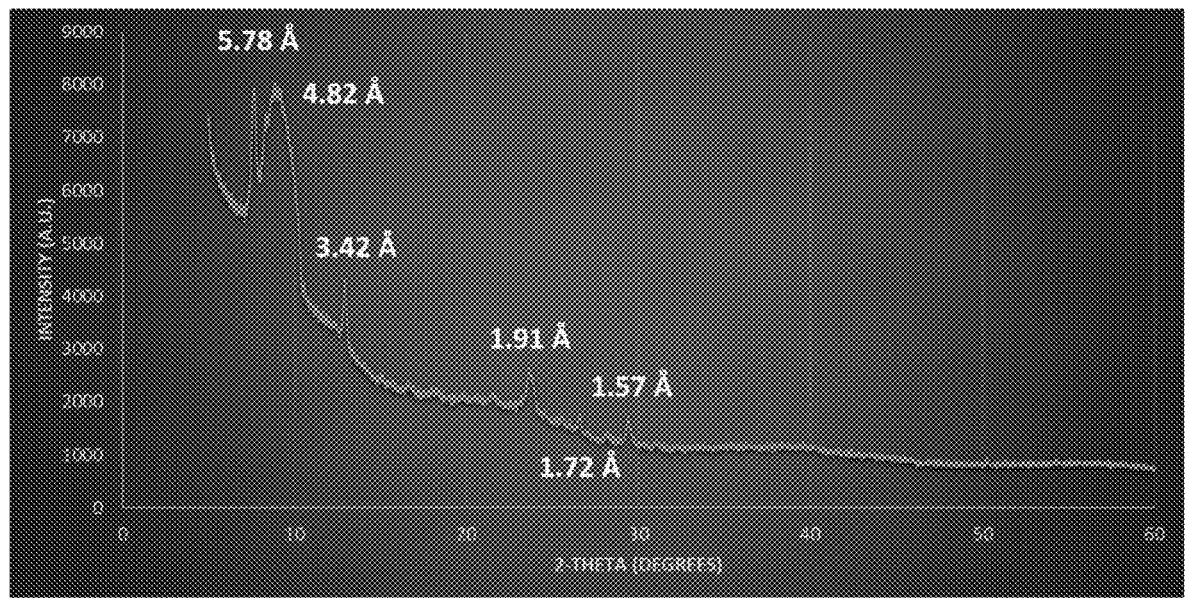
Fig. 4

FUNCTIONALIZED NANOPARTICLES HAVING ENCAPSULATED GUEST CARGO AND METHODS FOR MAKING THE SAME

CROSS-REFERENCE TO RELATED APPLICATIONS

The present application is a Continuation-in-Part of U.S. patent application Ser. No. 15/363,077, filed Nov. 29, 2016, which in turn claims priority to U.S. Provisional Patent Application Ser. No. 62/260,569, filed on Nov. 29, 2015.

FIELD OF THE INVENTION

The invention relates to the synthesis of cellulose acetate nanoparticles and rods which have various bulk and surface functionalities and which carry encapsulated cargo (i.e., physically encapsulated substances).

BACKGROUND FOR THE INVENTION

The first reported synthesis of cellulose acetate (CA) nanoparticles was performed in 2008. The ability of composite nanoparticles to encapsulate hydrophobic substances within aqueous media or by further surface functionalization possess potential utility in pharmaceutical and bio- or food technology. Beyond cellulose acetate, other polysaccharide nanoparticles including cellulose variants have been demonstrated for delivery and imaging; each approach retains specific strengths, weaknesses, forms, and applications. No known methods and/or resulting particles exhibit the size, surface functionality, and cargo-carrying ability as the methods and resulting particles of the present invention.

SUMMARY OF THE INVENTION

This invention describes the synthesis of cellulose acetate nanoparticles having diameters ranging from 30-200 nm, and rods with diameters of 50 nm-10 microns having an aspect ratio of 100:1 and higher. We further disclose the use of the same in application, in which a desired functionality and encapsulated cargo load can be provided. Nonrestrictive examples include development of bright fluorescent nanoparticles and rods useful for imaging. While cellulose acetate is relatively hydrophobic overall, the ability of cellulose acetate to assemble into stable, nanoscale particles via precipitation techniques reflects amphiphilic functionality along the backbone. This heterogeneity enables cellulose acetate to interface with numerous polymers beyond functionalized, surface adsorbed polysaccharides. In general, the invention discloses the assembly of composite, surface-functionalized cellulose acetate nanoparticles. The following disclosure details particle morphological control, physical encapsulation range and extent, and non-covalent functionalization with multiple amphiphilic polymer co-assemblies.

Although the use of cellulose acetate is disclosed, the same method may be applied to any other derivative of cellulose that is soluble in organic solvents and sufficiently hydrophilic. Non-limiting examples include methylcellulose, ethylcellulose, propylcellulose, butylcellulose, cellulose acetate, cellulose propionate, cellulose butyrate, cellulose acetate butyrate, cellulose acetate propi-onate, methyl cellulose acetate, methyl cellulose propionate, methyl cellulose butyrate, ethyl cellulose acetate, ethyl cellulose propionate, ethyl cellulose butyrate, hydroxypropyl methylcellulose acetate, hydroxypropyl methylcellulose pro-pionate, and hydroxypropyl methylcellulose butyrate.

According to an embodiment of the invention, the process comprises:
(a) morphology control of the nanoparticles and rods precipitated by varying the solvent surface tension and polarity during nanoprecipitation synthesis.
(b) cargo loading by physical encapsulation of cargo guests of varying hydrophobicity; and
(c) functionalization of the particle surface, i.e. a non-covalent functionalization of the cellulose acetate nanoparticles or rods by a physical association with functionalizing molecules during the precipitation process, wherein said functionalizing molecules are amphiphilic in nature. Said functionalizing molecules comprise a surface functionalizing polymer, said surface functionalizing polymer is physically added to the synthesizing bath during the synthesis, and thus the nanoparticles precipitated comprise a functionalized surface because of the amphiphilic nature of the functionalizing molecules, said functionalizing molecules comprising two parts, a first part which is more hydrophilic, and a second part which is more hydrophobic. The more hydrophobic part of the functionalizing molecule associates with the cellulose acetate core of the nanoparticle.

The present invention, as disclosed, comprises both a (nano)particle and methods for making the same (nano)particle.

In particular, the present invention comprises a particle, comprising cellulose acetate, functionalizing molecules (more hydrophilic part of at least one surface functionalizing polymer), wherein said surface functionalizing polymer is non-covalently (i.e. physically) bonded to the cellulose acetate, and a cargo agent, wherein the cargo agent is non-covalently (i.e. physically) bonded to the cellulose acetate.

In some aspects, said surface functionalizing polymer is present on the particle surface, thereby functionalizing the particle surface. In some aspects, said surface functionalizing polymer comprises amphiphilic molecules. In some aspects, said surface functionalizing polymer is either an ionic surfactant, a non-ionic surfactant, or a charged polyelectrolyte. In some aspects, the particle has a surface chemistry, said surface chemistry being defined by a presence of surface hydroxyl groups. In some aspects, the particle has a surface chemistry, said surface chemistry being defined by a presence of surface amino groups.

In some aspects, the cargo agent is fluorescent. In some aspects, the method produces particles exhibiting fluorescent ultrabrightness. In some aspects, the particle exhibits fluorescence in the near infrared part of the spectrum.

In some aspects, the guest cargo includes various biological active compounds, in particular, drugs, dissolvable in the organic solvent that dissolves cellulose acetate.

In some aspects, the cargo agent dictates a core crystallinity of the particle.

In some aspects, the particle has a sphere-like shape. In some aspects, the particle has a rod shape. In some aspects, the particle has an average size ranging from 30 to 500 nm. In some aspects, the particle has a shape, the shape being an ellipse, an oval, a sphere or spheroid, a sheet, or a branch.

Also disclosed is a method for making the particle, preparing a first medium, the first medium comprising: dissolving cellulose acetate in an organic solvent, dissolving or dispersing a guest cargo in said organic solvent, by adding said cellulose acetate, and said guest cargo in said organic solvent; preparing a second medium, the second medium comprising a miscible non-solvent; adding at least one surface functionalizing polymer to either of said two media or both media, combining both said media by mixing, precipitating one or more particles, and removing said organic solvent, each particle comprising said cellulose acetate, surface functionalizing molecules of said surface functionalizing polymers, and said guest cargo, wherein said precipitating particle forms non-covalent bonds between said cellulose acetate and said guest cargo.

In some aspects, the solvent is removed via vacuum. In some aspects, the solvent is removed via dialysis.

In some aspects, the guest cargo is a fluorescent dye.

In some aspects, the guest cargo includes various biological active compounds, in particular, drugs, dissolvable in the organic solvent that dissolves cellulose acetate.

In some aspects, the particle further comprises a surface functionalizing polymer that is physically bonded to the cellulose acetate. In some aspects, the surface functionalizing polymer is present on the particle surface, thereby functionalizing the particle surface.

In some aspects, the surface functionalizing polymer is either an ionic surfactant, a non-ionic surfactant, or a charged polyelectrolyte. In some aspects, the particle has a surface chemistry, said surface chemistry being defined by a presence of surface hydroxyl groups. In some aspects, the particle has a surface chemistry, said surface chemistry being defined by a presence of surface amino groups.

In some aspects, the guest cargo dictates a core crystallinity of the particle.

In some aspects, the particle (or the method produces a particle which) has a spherical/spheroid shape. In some aspects, the particle has a rod shape. In some aspects, the particle has an average size ranging from 30 to 200 nm. In some aspects, the particle has a shape, the shape being a sheet or a branch.

The organic solvent can be chosen of a family of low-polarity solvents capable of dissolving cellulose acetate. In some aspects, the organic solvent possesses a polarity index between 4 and 7.5.

In some aspects, a nature of the organic solvent determines at least one of: particle size, particle surface chemistry, and particle core crystallinity.

In some aspects, a nature of the guest cargo determines at least one of: particle size, particle shape, particle surface chemistry, and particle core crystallinity.

In some aspects, the method further comprises the step of adding a surface functionalizing polymer. In some aspects, the surface functionalizing polymer is present on the particle's surface, thereby functionalizing the particle. In some aspects, the surface functionalizing polymer is an ionic surfactant, a non-ionic surfactant, or a charged polyelectrolyte. In some aspects, the surface functionalizing polymer determines at least one of: particle size, particle surface chemistry, and particle core crystallinity.

BRIEF DESCRIPTION OF DRAWINGS

FIGS. 3A-3B. Examples of the nanoparticles synthesized according to the present invention.

FIG. 3A. 1×1 µm$^2$ AFM image of cellulose acetate nanoparticle; inserted image is a 170×270 nm$^2$ image showing the spherical geometry of the particles;

FIG. 3B. 25×25 µm$^2$ fluorescent image of single particles having encapsulated fluorescent cargo.

FIG. 4. An exemplary x-ray analysis of the cellulose acetate nanoparticles according to the present invention.

FIG. 5A demonstrates the diversity in needle morphology from a single assembly. FIG. 5B illustrates a bundle of smaller, more homogeneously sized needles.

DETAILED DESCRIPTION OF PREFERRED EMBODIMENTS

Definitions

The terms not specifically defined here are generally used terms in their corresponding sciences. For example, in dynamic light scattering technique, the number average particle size is defined as the most probable particle size (mode of the particle size distribution), whereas the effective diameter is defined as the average diameter of the particles (mean of the particle size distribution). By default, the particle size term means the most probable particle size.

It should be noted that the term "physical encapsulation" is synonymous with "non-covalent encapsulation," as the terms are both used herein. Physical or non-covalent encapsulation means the entrapment by means of physical or noncovalent bonds (forces). The terms physical and noncovalent bonds/forces are used here in a generally accepted way in chemistry, see, for example, classification of intermolecular forces in Israelachvili, Intermolecular and Surface Forces, 3$^{rd}$ edition 2011 Elsevier Inc.

The fluorescent brightness of a fluorescent particle is referred to as "fluorescent ultrabrightness" (or, simply, "ultra-bright" or "ultrabright") when the brightness of the particle is higher than the maximum fluorescent brightness coming from a particle of the same size and comprising quantum dots of a similar spectrum encapsulated in a polymer matrix.

Reference in this specification to "one embodiment," "an embodiment," "one version," "a version," should be understood to mean that a particular feature, structure, or characteristic described in connection with the version, or embodiment is included in at least one such version, or embodiment of the disclosure, and may be included in more than one embodiment or version. The appearances of phrases "in one embodiment", "in one version," and the like in various places in the specification are not necessarily all referring to the same version, or embodiment, nor are separate or alternative versions, variants or embodiments mutually exclusive of other versions, variants, or embodiments. Moreover, various features are described which may be exhibited by some versions, or embodiments and not by others. Similarly, various requirements are described which may be requirements for some versions, variants, or embodiments but not others. If the specification states a component or feature "may", "can", "could", or "might" be included or have a characteristic, that particular component or feature is not required to be included or have the characteristic.

Furthermore, as used throughout this specification, the terms 'a', 'an', 'at least' do not denote a limitation of quantity, but rather denote the presence of at least one of the referenced item, and any usage of the term 'a plurality' denotes the presence of more than one referenced items.

Method of Assembly of the Particles.

Figure 2:
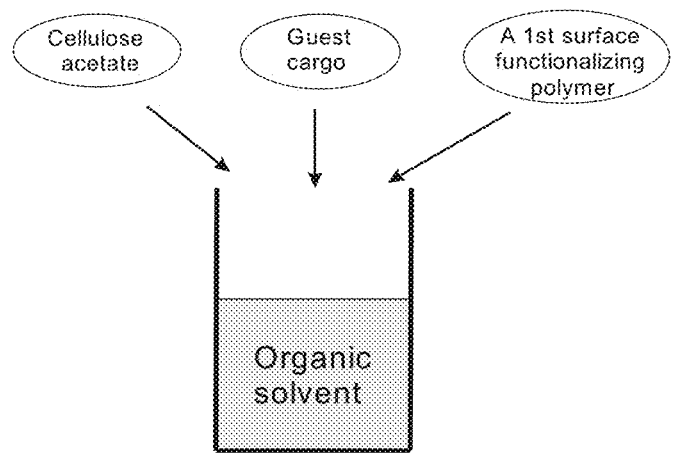
FIG. 2. A general diagram of the disclosed method is shown.
Figure 2:
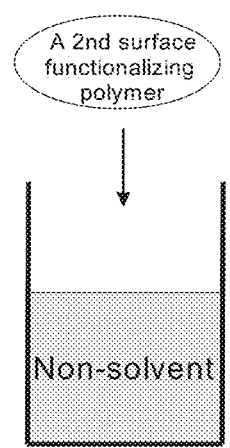
Figure 2:
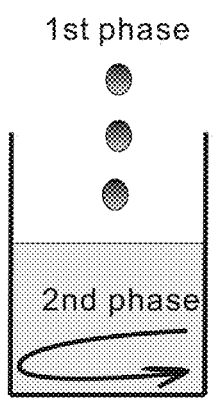
Figure 2:
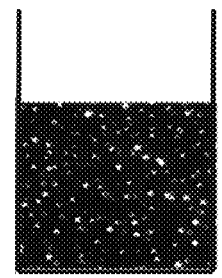
Figure 2:
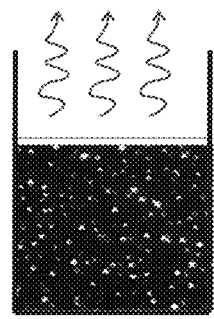

FIG. 2 summarizes the disclosed process via illustration. The method comprises five steps numbered for convenience of presentation.

Step 1: Preparing a first medium, comprising: dissolving a cellulose acetate in an organic solvent, dissolving or dispersing a guest cargo in said organic solvent, dissolving a first surface functionalizing polymer in said organic solvent, mixing said guest cargo with set cellulose acetate and said first surface functionalizing polymer in said organic solvent to form a mixture. The organic solvent can be chosen of a family of low-polarity solvents capable of dissolving cellulose acetate. Non-restrictive examples include hexane, acetone, Tetrahydrofuran (THF), dimethyl sulfoxide (DMSO), dimethylformamide (DMF), methanol, ethanol, n-propanol, isopropanol, and chloroform. The preferable organic solvent possesses a polarity index between 4 and 7.5. Said guest cargo determines the bulk (i.e. inner volume) functionality of the particles, such as fluorescence or biomedical activity. Said first surface functionalizing polymer provides for the surface functionality, such as a definite surface charge (zeta potential) and/or an increase or decrease in the particle's adhesion to specific molecules/surfaces.

Step 2: Preparing a second medium, said medium comprising: a non-solvent miscible with said solvent of Step 1. Said non-solvent is chosen from a family of high polarity solvents having poor solubility of said cellulose acetate. Non-restrictive examples include water, an alcohol, or a water/alcohol combination. Then, optionally, dissolving a second surface functionalizing polymer. Said second surface functionalizing polymer is added to provide for an additional surface functionality, such as a definite surface charge (zeta potential) and/or an increase or decrease in the particle's adhesion to specific molecules/surfaces.

Step 3: Combining the solution of the first medium (i.e. Step 1, above) and the solution of the second medium (i.e. Step 2, above); the process is exampled in FIG. 2 by drop wise adding the first medium into the second one, with subsequent mixing/stirring the obtained solution.

Step 4: Precipitating one or more particles. Each particle precipitated comprises said cellulose acetate, said guest cargo dispersed in said cellulose acetate, said guest cargo being non-covalently bonded to and dispersed within said cellulose acetate, a coating, the coating comprising said functionalities of said surface functionalizing polymers non-covalently bonded to said cellulose acetate, and a functionalized surface due to said coating, such that a surface of said precipitated particles is functionalized.

Step 5: Removal of organic solvent by vacuum drying and/or dialysis. Said assembled/precipitated particles are thus dispersed in a nonsolvent medium.

Particle Morphology Control.

Nanoparticles. Cellulose acetate nanoparticle morphologies are broadly manipulated by controlling initial polymer dispersity and the interface between polymer/solvent and miscible non-solvent. Polymer affinity, polarity, and surface tension are all physical properties of organic solvents that directly influence particle size and its polydispersity (polydispersity, as used herein, is defined as the broadness of the synthesized particle size distribution; the more broad, the larger the polydispersity). The Gibbs-Marangoni effect and supersaturation are regarded as relatively comprehensive models of nanoprecipitation with polymeric materials. While these theories are consistent with most syntheses, assembly inconsistencies have been observed. Such inconsistencies affect morphology control depending on the direction of the nanoprecipitation interface and polymer-solvent similarities. For example, the addition of dissolved polymer in acetone added to hexane versus water produces significantly different sizes despite similar polarity differences—290 nm (effective diameter for hexane) vs. 60 nm (effective diameter for water).

Figure 1A:
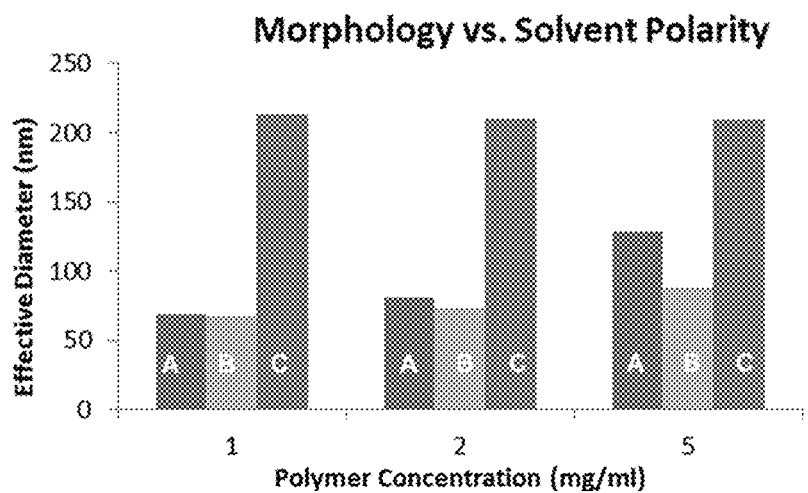
FIG. 1A. The dependence of particle morphology of the solvent. The effective diameters of cellulose acetate particles are shown as a function of polymer concentration and solvent polarity. In this Figure, 'A' stands for DHF, 'B' for acetone, and 'C' for DMSO.
Figure 1B:
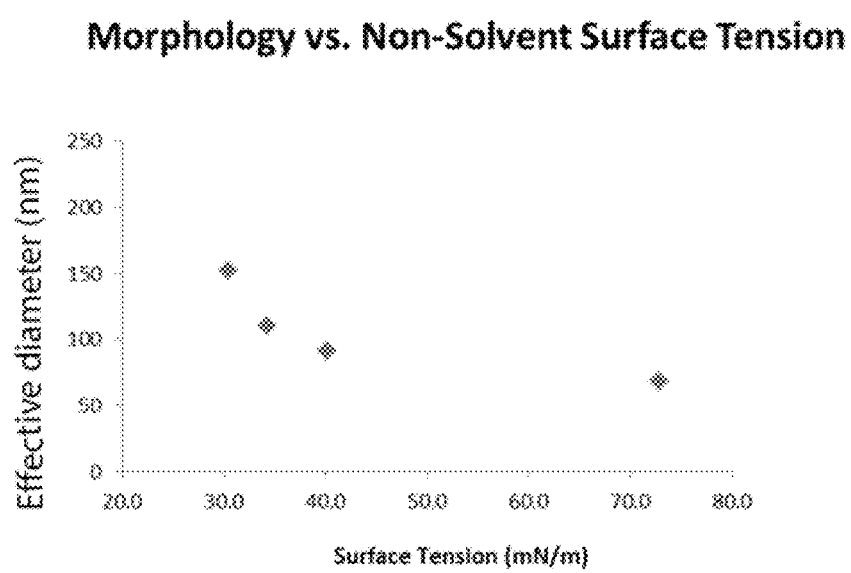
FIG. 1B. The effective diameters of cellulose acetate particles synthesized when using different non-solvent surface tensions according to the present invention are shown.

In the present disclosure, the most probable particle size of the precipitated cellulose acetate nanoparticles ranges from 30-200 nm (number average) and 60-300 nm (effective diameter). Utilizing a dropwise adding (as opposed to a bulk solution mixing) of dissolved polymer solution, polydispersity index (PDI) spans from 0.10 to 0.24 without encapsulation of guest cargo and without post-synthesis filtering (which is typically used to decrease polydispersity). FIG. 1 illustrates the impact of solvent physical properties—specifically, polarity and surface tension—on cellulose acetate particle size. Control is exhibited across polymer concentration, polarities index, and surface tension. Preferable conditions are: 1-2 mg/ml polymer concentration, and a solvent polarity index from 4-5.5. (see FIGS. 1A-1B).

Table 1. The surface tension of several solvents is further specified in Table 1, below:

TABLE 1

| Solvent | Surface Tension (mN/m) |
| --- | --- |
| Hexane | 18.43 |
| Acetone | 25.20 |
| THF | 26.40 |
| DMSO | 43.54 |
| Water | 72.80 |

Table 1 shows the range of surface tensions suggesting direction of interfacial movement during precipitation.

Another morphology control method includes the use of a surface functionalizing polymer and encapsulated guest cargo. This is described later in this description.

Synthesis of Rod-Like Particles or Structures (i.e. Rods).

A certain type of guest cargo can substantially alter the particles shape, forming a rod-like structure rather than a sphere- or spheroid-like structure. As an example, a dye of a family of conjugated hydrophobic dyes, exampled by Nile Red dye, produces rod-shaped particles possessing high aspect ratios which may comprise tunable dimensions (for example, aspect ratios of 100:1 and above). Examples of such assembled rods feature a diameter as small as 50 nm and a length of 1-2 microns, however the rods may span to as large as several microns in diameter (1-150 microns) and several hundred microns in length (100+ microns). This invention represents the first case of this type of assembly (i.e. physical encapsulation creating non-covalent bonding) using cellulose acetate or any other cellulose variant. It should be noted that the process of physical encapsulation as described herein leads to a specific product of cellulose acetate (or other cellulose acetate variants) and a contrast agent (e.g. fluorescent dye), the cellulose acetate and the contrast agent being non-covalently bonded. Thus, the product and process of synthesizing the product are one and the same because the process only creates the nanoparticles claimed, and the nanoparticles claimed are a result of only the process claimed. A different process would lead to a different structure than that claimed hereinbelow.

Figures 5A, 5B:
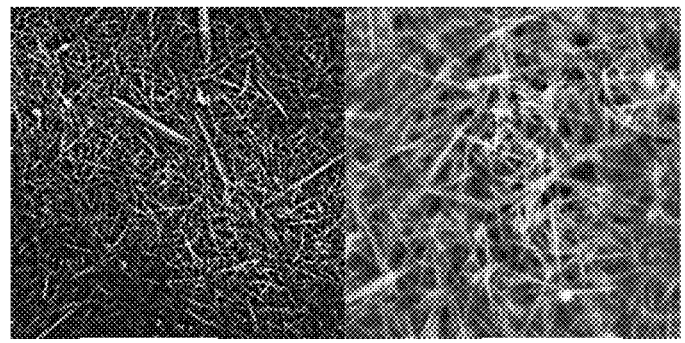
FIGS. 5A-5B. SEM images of cellulose acetate rods with 20:1 aspect ratio.
Figures 6A, 6B:
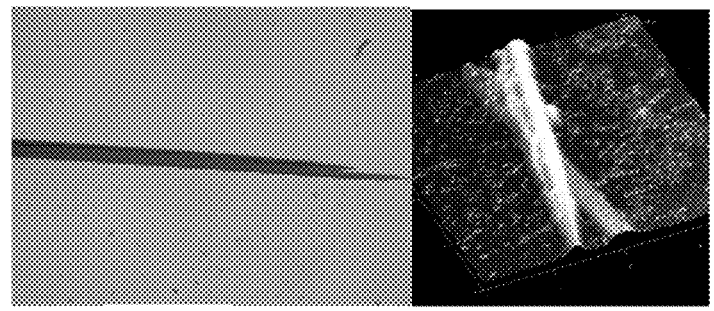
FIG. 6A. A cross-polarized microscope image of the end of a cellulose acetate microneedle assembled according to the present invention at a bulk scale. The total needle length is several hundred microns.
FIG. 6B. An atomic Force Microscopy (AFM) three-dimensional image showing the representative topology of a 300 nm-wide needle.

FIG. 5 shows Scanning Electron Micrographs (SEMs) of cellulose acetate-Nile Red composite rod-shape particles. The rods range from less than about 50 nm in diameter (see FIG. 5B) to about 200-300 nm (see FIG. 5A). Lengths span from 1 to 8 μm. FIG. 6A represents a cross-polarized image of a cellulose acetate rods grown in bulk. These rods are several hundred microns in length and possesses a smooth, transparent surface. FIG. 6B examples an Atomic Force Microscopy (AFM) image of two rods laying across one another.

FIG. 5 shows an SEM of cellulose acetate rods having a 20:1 aspect ratio. FIG. 5A demonstrates the diversity in needle-like (i.e. rod) morphology from a single assembly (i.e. a single synthesis). FIG. 5B illustrates a bundle of smaller, more homogeneously sized needle-like rod structures.

FIG. 6A shows a cross-polarized microscope image of the end of a cellulose acetate microneedle assembled at a bulk scale. The rod lengths are several hundred microns. FIG. 6B is an AFM image showing the representative topology of a 300 nm wide rod-like particle (top). The rod possesses a folded or tube-like structure, presumably having a hollow center, and while the top rod shown is tapered, the bottom particle shown has a flatter topography.

Encapsulation of Guest Cargo within Cellulose Acetate.

Cellulose acetate is capable of physically encapsulating guest cargo having a wide range of hydrophobicity/hydrophilicity. The type of guest cargo defines future application of the particles. For example, guest cargo may extend to therapeutic drug delivery applications, or for fluorescent tagging/imaging.

Therapeutic drug delivery may be exampled but are not limited to compounds for use in the following therapeutic areas: anticancer, antihypertensives, antianxiety agents, antiarrythmia agents, anticlotting agents, anticonvulsants, blood glucose-lowering agents, decongestants, antihistamines, antitussives, antine-oplastics, beta blockers, anti-inflammatories, antipsychotic agents, cognitive enhancers, anti-atherosclerotic agents, cho-lesterol-reducing agents, triglyceride-reducing agents, anti-obesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, and antiviral agents.

Exemplary guest cargo may include, but is not limited to, doxorubicin, camptothecin phosphodiesterase inhibitors, such as sildenafil and sildenafil citrate; HMG-CoA reductase inhibitors, such as atorvastatin, lovastatin, simvas-tatin, pravastatin, fluvastatin, rosuvastatin, itavastatin, nisv-astatin, visastatin, atavastatin, bervastatin, compactin, dihydrocompactin, dalvastatin, fluindostatin, pitivastatin, and velostatin (also referred to as synvinolin); vasodilator agents, such amiodarone; antipsychotics, such as ziprasidone; cal-cium channel blockers, such as nifedipine, nicardipine, vera-pamil, and amlodipine; cholesteryl ester transfer protein (CETP) inhibitors; cyclooxygenase-2 inhibitors; microsomal triglyceride transfer protein (MTP) inhibitors; vascular endothelial growth factor (VEGF) receptor inhibitors; car-bonic anhydrase inhibitors; and glycogen phosphorylase inhibitors.

The encapsulation efficiency of guest cargo using fluorescent dyes is described as an example. Any molecular fluorescent dye and/or their combinations may be used for this purpose. Both hydrophobic and hydrophilic dyes may be utilized.

The hydrophilic dyes applicable may be exampled by the following: the family of triarylmethane dyes (preferably s rhodamine dyes), Acridine dyes, Cyanine Dyes, Fluorone dyes, Luciferins, Oxazine dyes, Phenanthridine dyes, ATTO, DyLight dyes. A preferable set of dyes includes, but is not limited to, Rhodamine B, 6G, 640, Stilbene 420, Rhodamine 560, Methylene Blue, LD700, octadecyl ester, Cy3, Cy5, Cy3.5, Cy5.5, IR813, IR143, Indocyanine Green (ICG), and Fastblue fluorescent dyes.

The hydrophobic dyes may be exampled by the following: the family of commercially available hydrophobic fluorescent dyes, exampled by DayGlo® dyes (D-208 Apache Yellow®, D-098 Pocono Yellow®, D-063 Ozark Orange®, D-041 Grand Red®, D-838 Potomac Yellow®, D-149 Ottawa Red®), pyrene, hydrophobic fluorescent polymers are selected from poly[(9,9-dioctyl-2,7-divinylenefluorenylene)-alt-co-(9,10-anthracene)]; poly[(9,9-dioctyl-2,7-divinylenefluorenylene)-alt-co-{2-methoxy-5-(2-ethylhexyloxy)-1,4-phenylene}]; poly[(9,9-dioctyl-2,7-divinylenefluorenylene)-alt-co-(1,4-phenylene)]; poly[(9,9-dioctylfluorenyl-2,7-diyl)-alt-co-(1,4-benzo-{2,1',3}-thiadiazole)]; poly[(9,9-dihexylfluorenyl-2,7-diyl)-alt-co-(2-methoxy-5-{2-ethylhexyloxy}-1,4-phenylene)]; poly[(9,9-dioctylfluorenyl-2,7-diyl)-co-(2,5-p-xylene)]; poly[(9,9-dioctylfluorenyl-2,7-diyl)-co-(N,N'-diphenyl)-N,N-di(p-butylphenyl)-1,4-diamino-benzene)]; poly[(9,9-dioctylfluorenyl-2,7-diyl)-co-(1,4-benzo-{2,1',3}-thiadiazole)]; poly[2-methoxy-5-(2-ethylhexyloxy)-1,4-phenylene-vinylene], optionally end capped with dimethylphenyl; poly[2-methoxy-5-(2-ethylhexyloxy)-1,4-phenylene-vinylene], optionally end capped with polysilsesquioxane; poly[2-methoxy-5-(3,7-dimethyloctyloxy)-1,4-phenylene-vinylene], optionally end capped with dimethylphenyl; poly[2-methoxy-5-(3,7-dimethyloctyloxy)-1,4-phenylene-vinylene], optionally end capped with polysilsesquioxane; poly[9,9-dioctylfluorenyl-2,7-diyl], optionally end capped with dimethylphenyl; poly[9,9-dioctylfluorenyl-2,7-diyl], optionally end capped with polysilsesquioxane; poly[9,9-dioctylfluorenyl-2,7-diyl], optionally end capped with N,N-bis(4-methylphenyl)-aniline; poly[9,9-dioctylfluorenyl-2,7-diyl], optionally end capped with 2,5-diphenyl-1,2,4-oxadiazole; poly[9,9-di-(2-ethylhexyl)-fluorenyl-2,7-diyl], optionally end capped with dimethylphenyl; poly[9,9-di-(2-ethylhexyl)-fluorenyl-2,7-diyl], optionally end capped with polysilsesquioxane; poly[9,9-di-(2-ethylhexyl)-fluorenyl-2,7-diyl], optionally end capped with N,N-bis(4-methylphenyl)-aniline; poly[9,9-di-(2-ethylhexyl)-fluorenyl-2,7-diyl], optionally end capped with 2,5-diphenyl-1,2,4-oxadiazole; poly[2-(5-cyano-5-methylhexyloxy)-1,4-phenylene], optionally end capped with dimethylphenyl; and poly[2,5-dioctyl-1,4-phenylene], optionally end capped with dimethylphenyl; poly[9,9-di(3, 3'-N,N'-trimethyl-ammonium)propylfluorenyl-2,7-diyl]-alt-(9,9-dioctylfluorenyl-2,7-diyl)] diiodide salt, optionally end capped with dimethylphenyl; poly[2,5-bis(3,7-dimethyloctyloxy)-1,4-phenylene-vinylene]; poly(9,9-di{2-[2-(2-methoxy-ethoxy)ethoxy]ethyl}fluorenyl-2,7-diyl), optionally end capped with dimethylphenyl; and poly-BODIPY fluorescent polymers.

The synthesized cellulose acetate nanoparticles exhibit a degree of capturing anywhere from 100 to 450 dye molecules per normalized 40 nm diameter particle, based on absorbance and fluorescence measurements. Dyes remain associated well enough with the particle architecture such that high fluorescent signal remains despite diminishment in quantum yield. Further, the ability to capture such a large quantity of dye could be useful in photodynamic therapy (PDT). Table 2 (below) depicts the encapsulation ability of cellulose acetate nanoparticles with an FDA-approved IR dye, Indocyanine Green (IR125 or ICG). The number of dye molecules encapsulated per 40 nm diameter particle is assessed by comparing fluorescent intensity of particles versus free (i.e. unencapsulated) ICG in a water solution. It is notable that the effective amount of dye molecules encapsulated provides for fluorescent ultrabrightness (i.e., brighter than particles of similar fluorescent spectra assembled with quantum dots, or more simply, brighter than quantum dots).

TABLE 2

| Particle Type* | No. Dye Molecules** | Z-ave (nm) | PDI |
| --- | --- | --- | --- |
| 10E–6M IR125/TEA | 27 | 84 | 0.23 |
| 10E–2M IR125/TEA | 353 | 144 | 0.15 |

*2 mg/ml Cellulose
**Normalized to 40 nm diameter particle

Table 2 demonstrates the cellulose acetate nanoparticles' encapsulation ability using FDA-approved IR125. It appears that high encapsulation influences morphology. Generally, encapsulated particles range from 50 to 150 nm, number-based average (80-300 nm, effective diameter).

Figure 7:
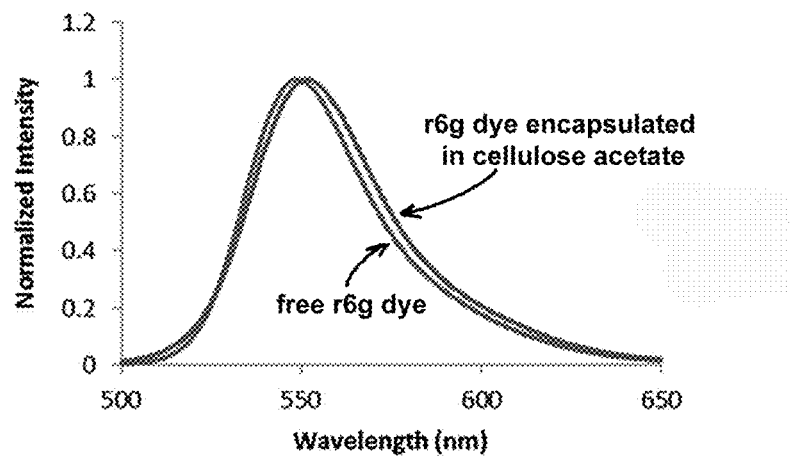
FIG. 7. Normalized intensity spectra of encapsulated R6G versus free R6G. The spectrum of encapsulated R6G appears slightly shifted (4 nm) and slightly broader. Excitation is performed at 488 nm.

FIG. 7 shows 2 spectra comparing encapsulated Rhodamine 6G (R6G) dye and free R6G in water. The fluorescent properties of R6G in encapsulated cellulose acetate particles demonstrate enough hydrophilic interaction between the core of the particle and dye to minimize quenching (quenching is defined herein as the disappearance of fluorescence). This is at least one of the mechanisms which provides for such ultrahigh brightness of the precipitated cellulose acetate nanoparticles comprising encapsulated fluorescent dyes.

Table 3. Brightness and morphology of nanoparticles produced, as a function of dye loading.

TABLE 3

| Concentration of SB | Size, Z (nm) | Size, Mn (nm) | Size, Std Dev (nm) | Brightness (dyes/40 nm) |
| --- | --- | --- | --- | --- |
| 2E–6M | 89 | 51 | 16.06 | 11 |
| 2E–5M | 93 | 53 | 17.18 | 30 |
| 2E–4M | 92 | 48 | 15.23 | 91 |
| 2E–3M | 93 | 50 | 16.55 | 272 |

Table 3 demonstrates the change of morphology of the particles, as well as their brightness (in the units of effective fluorescent brightness of individual free dye molecules), when using different concentrations of a dye when mixed with the organic solvents. The example of Stilbene 420 (SB) dye is given in this Table.

Figure 8:
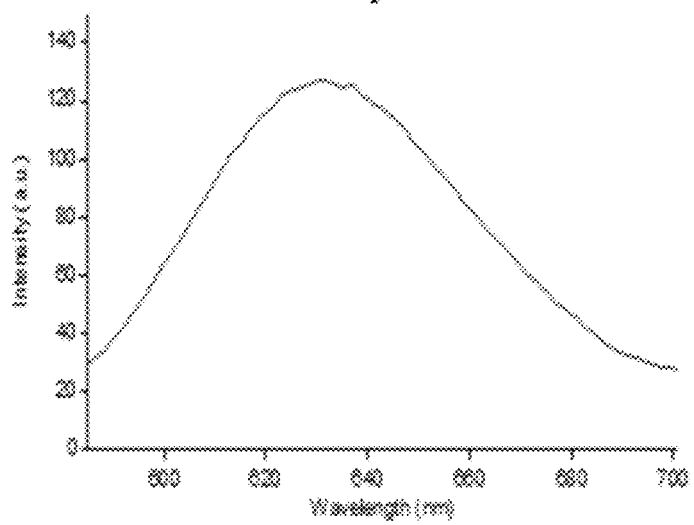
FIG. 8. Nile Red spectrum. Excitation is performed at 550 nm.

As described hereinabove, Nile Red dye, a lipophilic dye with a low solubility in water, exhibits a strong fluorescence when encapsulated. While cellulose acetate can be used to encapsulate hydrophilic dyes, it is ideally suited for hydrophobic guest encapsulation. FIG. 8 shows a Nile Red dye fluorescent spectrum when excited with light having a 550 nm wavelength.

Figure 9:
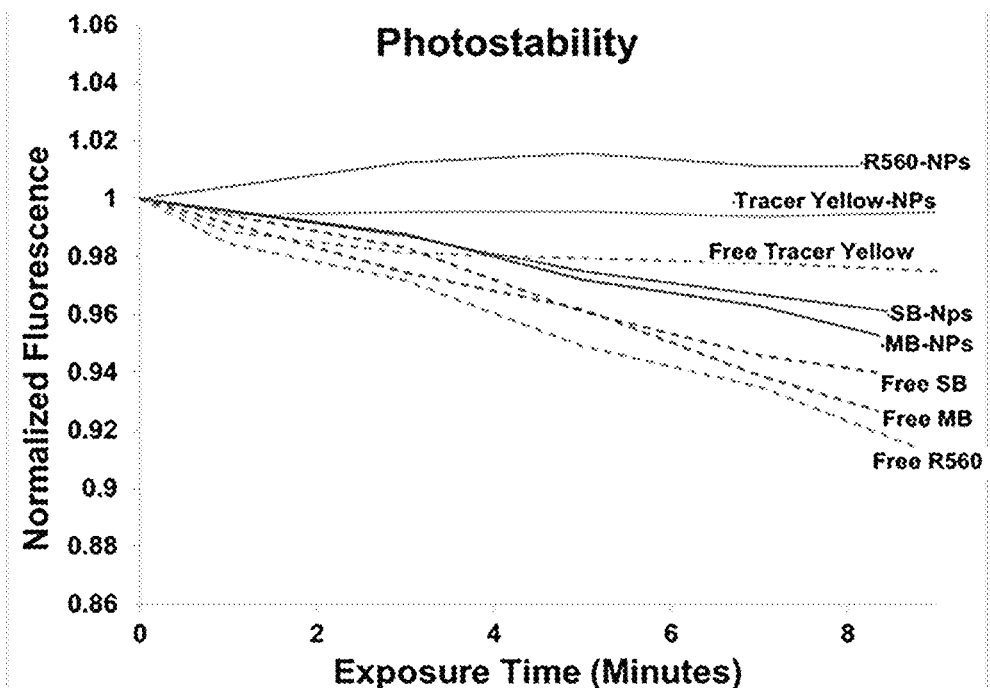
FIG. 9. Graphical representation of the photostability of incapsulated fluorescent dye versus free dye (i.e. unencapsulated dye) as a function of the exposure time.

An additional important property of the fluorescence of the cellulose acetate particles, as described herein, is an excellent photostability, or resistance to photobleaching compared to pure dye. FIG. 9 demonstrates an example of encapsulation of Stilbene 420, Rhodamine 560, Tracer Yellow, and Methylene Blue fluorescent dyes in a cellulose acetate nanoparticle matrix. The increased photostability of the dyes after encapsulation is clear from the Figure. Furthermore, FIG. 9 shows the higher photostability of encapsulated dye versus free (unencapsulated) dye, a greater normalized integrated fluorescence over time of the cellulose acetate nanoparticles comprising encapsulated dye. A short time exposure is shown in which photodegradation kinetics are comparable (relative beaching <10%). The example is of cellulose acetate nanoparticles comprising encapsulated Stilbene 420, Rhodamine 560, Tracer Yellow, and Methylene Blue fluorescent dyes (See FIG. 9).

Photostability measurements are performed by illuminating 3 mL of fluorescent nanoparticle solutions having the same optical density of 0.01 with white light from a 450 W xenon lamp. Simultaneously monitoring of intensity is performed with a Horiba Fluorolog 3 (Horiba, Japan) fluorimeter. Optical densities of the fluorescent unencapsulated dye and particles are chosen to have the same 0.01 absorbance. The solutions are separately irradiated continuously using the white light source and a slit width of 14.7 nm. For comparison, a 1 nm slit width is generally used when performing standard fluorescence measurements. Initial fluorescence intensity is recorded at time zero and represents the maximum intensity. Fluorescence is recorded every 60 seconds following continuous exposure and is normalized by the maximum intensity to produce a measure of percentage of fluorescence remaining. Photostability measurements are performed for 10 minutes, or according to the linear kinetic range of photodegradation (i.e. up to 80-90% of the initial fluorescence).

Functionalization of the Surface of the Precipitated Nanoparticles via Addition of a Specific Surface Functionalizing Polymer.

It is common in polymeric nanoparticles to conjugate drugs, contrast agents, and biostability enhancing molecules/polymers, like Polyethylene Glycol (PEG), chemically to the backbone prior to assembly. The present invention discloses a non-covalent functionalization of cellulose acetate particles by a physical association during the precipitation process via addition of a surface functionalizing polymer having a function. This may be done using amphiphilic molecules, one part of which includes a hydrophobic block, such as poly(propylene oxide), poly(lactic acid), poly(lactic-co-glycolic acid), poly(caprolactone), or combinations thereof. The other portion of the molecule can include a hydrophilic block, such as polyethylene glycol (PEG), poly(aspartic acid), poly(glutamic acid), or combinations thereof. Such amphiphilic molecules may be chosen from a range of polymers including ionic and non-ionic surfactants, block copolymers, and charged polyelectrolytes. For example, the block copolymer may comprise poly(aspartic acid)-6-poly(lactic acid)-6-poly(aspartic acid), poly(sebacic acid), Polyvinylpyrrolidone (PVP), poloxamer 407 (PF-127), and Polyethyleneimine (PEI).

The choice of a specific surface functionalizing polymer determines nanoparticle surface properties such as zeta potential (the surface charge). For example, branched 10K MW PEI, a cationic polymer containing primary, secondary, and tertiary amines, electrostatically anchors into the negatively charged cellulose acetate particle when added as a second surface functionalization polymer (added to the nonsolvent medium, Step 2), producing a positively charged shell (positive zeta potential). Although the surface functionalization polymer is added to the nonsolvent phase here, it may be added to either phase. The particle architecture retains a hydrophobic core while exposing reactive primary amines to the aqueous environment. In addition to enhancing stability, the potential of this approach for further surface modification will be apparent to those skilled in the art. The primary amines may be used as anchors to attach a large family of known functional molecules employing basic and standard chemistry. There are numerous synthetic chemical groups that will form chemical bonds with primary amines. These include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugates to amines by either acylation or alkylation. As an example, addition of reactive NETS-PEG ester effectively conjugates to the surface, PEGylating particles and improving stability and suitability of such particles for in-vivo applications.

Various examples are provided below which further specifically illustrate the methods and particles according to the present invention.

Example 1. Synthesis of Cellulose Acetate Nanoparticles for a Range of Parameters Cellulose acetate nanoparticles are prepared by nanoprecipitation. The first medium is prepared using 1 or 2 mg/ml of 50,000 MW cellulose acetate, which is dissolved in solvent (preferably, tetrahydrofuran or acetone) and added drop wise into the miscible non-solvent (preferably, water) at a 5:1 water to organic ratio (preferable range is from 3:1 to 6:1 water to organic ratios). Polymer solution addition rates span preferably from 1 ml/min to 5 ml/min, and are done so under vigorous stirring. Solvent is removed either under vacuum overnight or by dialysis. For dialysis, a cellulose membrane (Spectra/Por) with 12-14 KD cutoff is preferable. Particles are dialyzed according to standard practices. The average particle sizes obtained from this process range from 30 to 200 nm in diameter.

Example 2. A Second Synthesis of Cellulose Acetate Nanoparticles for Specific Applications The first medium is prepared using 1 mg/mL cellulose acetate (CA) solution, the CA solution comprising 30,000 MW CA (Sigma-Aldrich), and an organic solvent, the organic solvent comprising an equal mix of DMSO/THF/acetone, mixing the CA solution and solvent via stirring and sonication at room temperature for 3 hours. Separately, the second medium, non-solvent medium is prepared using water and a water-soluble surface functionalizing polymer, PF-127, and mixing with stirring for 2 hours to reach a final water-soluble surface functionalizing polymer concentration of 0.49 mg/mL. The first medium solution is introduced into the non-solvent medium under high agitation. The combined solution is stirred for 12 hours at room temperature. Solvent removal is initiated by placing the mixture under vacuum at 50 degrees Celsius. Trace solvent is removed by dialyzing the nanoparticle solution for 4 days with dialysate, changing every 3 hours for the first 2 days (every 6 hours during nights) and every 12 hours thereafter. Large particulates are removed with a 450 nm pore size syringe filter. In the specific synthesis, the reported average particle size is 51 nm (the number average), and the effective diameter is 80 nm. Said reported values were obtained using dynamic light scattering and atomic force microscopy.

To measure the particle size, the obtained nanoparticles were characterized using standard methods of dynamic light scattering and atomic force microscopy, as described below.

Dynamic Light Scattering (DLS) and zeta-potential measurements were conducted in DI water on a Malvern Zetasizer Nano ZS instrument after equilibration at 25 C. 0.1 mg/ml nanoparticle concentration was used for both size and zeta potential measurements.

Atomic Force Microscopy. Bioscope Catalyst (Bruker/Veeco, Inc., Santa Barbara, CA) atomic force microscope equipped with Nanoscope V controller was used in the study. Standard AFM cantilever holders for operation in air were employed. The particles were immobilized on glass slides prepared as follows. Glass slides were placed in an ethanol bath and sonicated for 15 minutes in order to cleanse the surface. Following washing, slides were dried under forced nitrogen gas. Poly-l-Lysine coating was applied to the glass slides via a standard Sigma-Aldrich protocol. In short, the 0.1% w/v poly-l-Lysine solution was diluted 1:10 with deionized water. This working solution was stored in a refrigerator at 2-8° C. and allowed to come to room temperature when used. Glass slides were incubated in the poly-l-Lysine solution for 5 minutes, drained and washed with DI water, and dried overnight at room temperature. Then a drop of 0.1 mg/ml solution of nanoparticles was dispensed on the slide and incubated for 60 minutes to allow electrostatic attachment of negatively-charged particles to the positively-charged glass surface. AFM imaging was performed once slides were washed and dried. FIG. 3 a shows an example of a family images of cellulose acetate nanoparticles.

The particle crystallinity can be identified by using, for example, x-ray scattering. FIG. 4 shows an example of x-ray analysis of cellulose acetate particles. Specific peaks in the scattered intensity indicate the presence of ordered structure, which is an indication of crystallinity.

Example 3. Synthesis of Cellulose Acetate Rods

To prepare the first medium, 1 or 2 mg/ml of 50,000 MW cellulose acetate is dissolved in an organic solvent, said organic solvent being capable of dissolving both cellulose acetate and Nile Red dye. The mixture is added dropwise (preferably 1-5 ml/min) into water (i.e. the second, nonsolvent medium) at a preferable ratio of 5:1 water to organic coupled with stirring. The rod assemblies begin to grow after about 30 seconds to 2 minutes post-precipitation. Solvent is removed either under vacuum or by dialysis. For dialysis, a cellulose membrane with 12-14 KD cutoff is used. Particles are dialyzed using standard practices. Due to the small solubility of Nile Red dye in water, removal of solvent can cause free (i.e. unencapsulated) Nile Red to precipitate out of the solution. These Nile Red precipitates can be filtered out using standard filtration, for example, using filter paper having a preferable pore size of 5 microns or larger.

Example 4. A Specific Example of Encapsulation of Fluorescent Dyes in Cellulose Acetate Nanoparticles The first medium is prepared with a 1 mg/mL cellulose acetate (CA) solution, the CA comprising 30K MW CA (Sigma-Aldrich), the CA being dissolved in an organic solvent, the organic solvent comprising an equal mix of DMSO/THF/acetone, the combining being via a stirring and sonication at room temperature for 3 hours. Stilbene 420 (blue), Rhodamine 560 (green), Tracer Yellow (yellow), or Methylene Blue (red/NIR) fluorescent dyes are used for encapsulation within the nanoparticles precipitated. Separately, the second (non-solvent) medium is prepared using water and a water-soluble surface functionalizing polymer, PF-127, and stirring the mixture for 2 hours to reach a final polymer concentration of 0.49 mg/mL. The first medium solution is introduced into the second (non-solvent) medium under stirring. The combined solution is allowed to stir for 12 hours at room temperature. Solvent removal is initiated by placing the mixture under vacuum at 50 degrees Celsius. Trace solvent is removed by dialyzing the nanoparticle solution for 4 days with dialysate, changing the dialysate every 3 hours (every 6 hours during nights), and every 12 hours thereafter. Large particulates are removed with a 450 nm pore size syringe filter (Pall Acrodisc). The solvent is removed by placing the mixture under vacuum at 50 degrees Celsius. Trace solvent and free unencapsulated dye are removed by dialyzing the nanoparticle solution for 4 days with dialysate, changing the dialysate every 3 hours (every 6 hours during nights) for the first 2 days, and every 12 hours thereafter. Dialysis is complete when no fluorescence of non-encapsulated dyes is present in the dialysate.

Table 4 shows the results of the synthesis of the cellulose acetate nanoparticles of the present invention comprising encapsulated dyes. Each nanoparticle demonstrates ultra-brightness, i.e., a higher brightness comparable to a quantum dot of similar brightness.

Table 4. Physical parameters of the synthesized cellulose acetate particles: size, the parameter characterizing polydispersity in size (PID), excitation/emission fluorescent maxima, fluorescent brightness, the zeta potential. Brightness relative to quantum dots is calculated for [1] QD450 (brightness $1 \times 10^5$ $M^{-1}$ $cm^{-1}$), [2] QD525 (brightness $1.3 \times 10^5$ $M^{-1}$ $cm^{-1}$), [3] QD585 (brightness $3.05 \times 10^5$ $M^{-1}$ $cm^{-1}$), [4] QD705 (brightness $1.2 \times 10^6$ $M^{-1}$ $cm^{-1}$).

Example 5. A Specific Example of Encapsulation of an Anticancer Drug, Doxorubicin, in Cellulose Acetate Nanoparticles The first medium is prepared with a 1 mg/mL cellulose acetate (CA) solution, the solution comprising 30,000 MW CA with an organic solvent, the organic solvent comprising an equal mix of DMSO/THF/acetone, the combining being performed via stirring and sonication at room temperature for 3 hours. Doxorubicin sodium salt is added to the first medium as a guest cargo. Separately, the second (non-solvent) medium is prepared using water and a water-soluble surface functionalizing polymer, PF-127, the preparing being via stirring for 2 hours to reach a final polymer concentration of 0.49 mg/mL. The first medium is introduced into the second medium under high agitation. The combined solution is allowed to stir for 12 hours at room temperature. Solvent removal is initiated by placing the mixture under vacuum at 50 degrees Celsius. Trace solvent is removed by dialyzing the nanoparticle solution for 1 hour. Large particulates are removed with a 450 nm pore size syringe filter. The obtained nanoparticles have a number average particle size of 72 nm and an average effective diameter of 109 nm; the nanoparticles have a PDI of 0.1.

Example 6. Functionalized Cellulose Acetate Particles

The first medium is created via dissolution of a 1-2 mg/ml solution of 50,000 MW cellulose acetate in an organic solvent as well as with an equal concentration (preferably 1:1) of a surface functionalizing polymer. Polyvinylpyrrolidone (PVP), Polyethyleneimine (PEI), Polyethyleneimine conjugated with PEG, and poloxamer 407 PF-127 are used as the surface functionalizing polymer. This mixture is added dropwise into a non-solvent second (aqueous) medium solution at a 5:1 ratio of aqueous to organic under vigorous stirring. If the guest cargo used for surface functionalization is insoluble or poorly soluble in the organic solvent, a mixed solvent mixture can be utilized. Solvent is removed either under vacuum overnight or by dialysis. For dialysis, a cellulose membrane (Spectra/Por) with 12-14 KD cutoff is used. Particles are dialyzed according to known standard protocols.

Table 5. The data showing the effect of introducing a surface functionalizing polymer to functionalize the particle surface, and providing a different zeta-potential.

TABLE 4

| Encapsulated dye | Size, (nm) | PDI | Ex/Em (nm/nm) | Brightness (MBTU)/M · $cm^{-1}$ | Brightness relative to QD (times) | Zeta-Potential (mV) |
|---|---|---|---|---|---|---|
| Stilbene 420 | 61 | 0.22 | 400/445 | 89 ± 4/ (5.8 ± 0.3) × $10^6$ | 58 [1] | −8.0 ± 1 |
| Rhodamine 560 | 77 | 0.13 | 495/525 | 870 ± 71/ (6.4 ± 0.5) × $10^7$ | 640 [2] | −17 ± 2 |
| Tracer Yellow | 60 | 0.15 | 450/560 | 159 ± 13/ (4.3 ± 04) × $10^6$ | 43 [3] | −3 ± 2 |
| Methylene Blue | 77 | 0.17 | 665/680 | 2554 ± 268/ (1.3 ± 0.1) × $10^8$ | 1300 [4] | −19 ± 1 |

TABLE 5

| Particle Type* | Z-ave (nm) | PDI | Zeta (mV) |
| --- | --- | --- | --- |
| Cellulose Acetate (2 mg/ml THF) | 81 | 0.19 | −28.1 |
| Cellulose-Polyvinylpyrrolidone (PVP) | 121 | 0.18 | −8.9 |
| Cellulose-Polyethyleneimine (PEI) | 119.5 | 0.15 | 47.8 |
| Cellulose-Polyethyleneimine/PEG | 116 | 0.14 | 26.0 |
| Cellulose-PF127 | 103 | 0.22 | −11.5 |

*2 mg/ml Cellulose; 1:1 Cellulose to Polymer Ratio except PEI

Table 5 shows the obtained cellulose acetate particles, their size, and their surface chemistry. The average particle size, polydispersity index, and zeta potential are shown. The table shows the different surface properties and particles morphology when using different surface functionalizing polymers.

Example 7. Synthesis of Cellulose Acetate Nanoparticles Carrying Fluorescent Guest Cargo and Comprising a Functionalized Surface with Folic Acid This example demonstrates a general approach of synthesizing the cellulose acetate nanoparticles by adding a fluorescent cargo and a first and second surface functionalizing polymers, to add a functional molecule to the particle surface. The first surface functionalizing polymer is copolymer PF-127, which adds polyethylene glycol functional molecules to the particle surface. The second surface functionalizing polymer is an amphiphilic conjugate between a hydrophobic block and hydrophilic functional molecules. Specifically, it is a conjugate of copolymer PF-127 and folic acid, PF-127-FA. The first medium is created by dissolving a cellulose acetate in DMSO/acetone (15:85 v/v). A 1 mg/mL cellulose acetate solution is prepared via stirring and sonication at room temperature for 3 hours. The guest cargo, fluorescent dyes Stilbene 420 (blue), Rhodamine 560 (green), Tracer Yellow (yellow), and Methylene Blue (red/NIR) were used for encapsulation. Introduction of each dye is described in the following example of Stilbene 420 dye. The first medium is created by dissolving of 1 mg of Stilbene 420 dye in said cellulose acetate solution, and subsequent dissolution of the first surface functionalizing polymer PF-127. The obtained mixture is stirred at room temperature for 30 minutes. The second medium is obtained dissolution of the second surface functionalizing polymer, 50 ul of (concentration 10 mg/mL) of PF-127-FA conjugate in deionized water (non-solvent phase) via stirring for 10 minutes. The first medium is combined with the second medium via stirring for 12 hours at room temperature. The solvent is removed by placing the mixture under vacuum at 50 degrees Celsius. Trace solvent and free dye are removed by dialyzing the nanoparticle solution for 4 days with dialysate, changing every 3 hours (6 hours during nights) for the first 2 days, and every 12 hours thereafter. Dialysis is complete when no fluorescence of non-encapsulated Stilbene 420 is present in the dialysate. Large particulates are removed with a 450 nm pore size syringe filter.

Table 6 shows the results of the synthesis of cellulose acetate particles with the encapsulated dyes and functionalized with additional surface functionalizing polymers, PEG part of PF-127 and folic acid part of the conjugate of PF-127. It can be seen from the Table that the encapsulated cargo produces ultrabright fluorescence (brighter than quantum dots of similar spectrum) as well as efficient functionalization with folic acid molecules and PEG.

The number of folic acid molecules is calculated using UV-VIS absorbance, and independently by Roman spectroscopy. Both techniques provide similar results.

Table 6. Physical parameters of the synthesized cellulose acetate particles with fluorescent cargo, the cellulose acetate particles further being functionalized with a first and second functionalizing polymers. Shown are the following: the size, the parameter characterizing poly-dispersity in size (PID), excitation/emission of fluorescent maxima, fluorescent brightness, the zeta potential, and the number of folic acid molecules per particle. Brightness relative to quantum dots was calculated for [1] QD450 (brightness $1 \times 10^5$ $M^{-1}$ $cm^{-1}$), [2] QD525 (brightness $1.3 \times 10^5$ $M^{-1}$ $cm^{-1}$), [3] QD585 (brightness $3.05 \times 10^5$ $M^{-1}$ $cm^{-1}$), QD705 (brightness $1.2 \times 10^6$ $M^{-1}$ $cm^{-1}$).

TABLE 6

| Encapsulated dye | Size, (nm) | PDI | Ex/Em (nm/nm) | Brightness (MBTU)/M · cm[1] | Brightness relative to QD (times) | Zeta-Potential (mV) | Number of folic acid molecules |
| --- | --- | --- | --- | --- | --- | --- | --- |
| Stilbene 420 | 61 | 0.22 | 400/445 | 89 ± 4/ (5.8 ± 0.3) × $10^6$ | 58 [1] | −8.0 ± 1 | 870 ± 220 |
| Rhodamine 560 | 77 | 0.13 | 495/525 | 870 ± 71/ (6.4 ± 0.5) × $10^7$ | 640 [2] | −17 ± 2 | 910 ± 200 |
| Tracer Yellow | 60 | 0.15 | 450/560 | 159 ± 13/ (4.3 ± 04) × $10^6$ | 43 [3] | −3 ± 2 | 1110 ± 180 |
| Methylene Blue | 77 | 0.17 | 665/680 | 2554 ± 268/ (1.3 ± 0.1) × $10^8$ | 1300 [4] | −19 ± 1 | 930 ± 290 |

The descriptions given here, while indicating various embodiments of the invention and numerous specific details thereof, are given by way of illustration and not of limitation. Many substitutions, modifications, additions and/or rearrangements may be made within the scope of an embodiment of the invention without departing from the spirit thereof, and embodiments of the invention include all such substitutions, modifications, additions and/or rearrangements.

It should also be noted that the term "comprising" does not exclude other elements or features and the "a" or "an" does not exclude a plurality. The verb 'comprise' and its conjugations do not exclude the presence of elements or steps other than those listed in any claim or the specification as a whole. The singular reference of an element does not exclude the plural reference of such elements and vice-versa. The mere fact that certain measures are recited in mutually different dependent claims does not indicate that a combination of these measures cannot be used to advantage. Furthermore, elements described in association with different embodiments may be combined. Finally, it should be noted that the above-mentioned examples, and embodiments illustrate rather than limit the invention, and that those skilled in the art will be capable of designing many alternative embodiments without departing from the scope of the invention as defined by the appended claims. As equivalent elements may be substituted for elements employed in claimed invention to obtain substantially the same results in substantially the same way, the scope of the present invention is defined by the appended claims, including known equivalents and unforeseeable equivalents at the time of filing of this application. Thus, in closing, it should be noted that the invention is not limited to the abovementioned versions and exemplary working examples. Further developments, modifications and combinations are also within the scope of the appended patent claims and are placed in the possession of the person skilled in the art from the present disclosure. Accordingly, the techniques and structures described and illustrated previously herein should be understood to be illustrative and exemplary, and not necessarily limiting upon the scope.

What is claimed is:

1. A method for precipitating one or more particles, comprising the steps of:
   preparing a first medium, preparing said first medium comprising the steps of:
      dissolving cellulose acetate in an organic solvent,
      dissolving or dispersing a fluorescent dye in said organic solvent
      dissolving a copolymer of poloxamer-based polymeric compound in said organic solvent,
      mixing said fluorescent dye, said cellulose acetate, and said copolymer of poloxamer-based polymeric compound in said organic solvent to form a mixture,
   preparing a second medium, preparing said second medium comprising the step of: dissolving a copolymer of poloxamer-based polymeric compound and a folic acid poloxamer-based polymeric compound conjugate in a non-solvent, said non-solvent being water; and
   mixing said first medium and said second medium,
   non-covalently bonding said copolymer of poloxamer-based polymeric compound and a folic acid of poloxamer-based polymeric compound conjugate to a surface of one or more cellulose acetate particles formed during the mixing, and
   precipitating one or more particles, each particle comprising:
      cellulose acetate,
      a coating,
      a functionalized particle surface due to said coating,
   wherein each precipitated particle has a spherical shape and a size of 50 nm to 87 nm, wherein the poloxamer-based polymeric compound is poloxamer 407.

2. The method for precipitating one or more particles according to claim 1 in which the folic acid poloxamer-based polymeric compound conjugate is folic acid-poloxamer 407 conjugate.

* * * * *